United States Patent [19]

Radding et al.

[11] Patent Number: 4,888,274
[45] Date of Patent: Dec. 19, 1989

[54] RECA NUCLEOPROTEIN FILAMENT AND METHODS

[75] Inventors: Charles M. Radding, Hamden; Saul M. Honigberg; Sherman Weissman, both of New Haven, all of Conn.; Basil Rigas, New York, N.Y.; Andrew A. Welcher, New Haven; David C. Ward, Guilford, both of Conn.

[73] Assignee: Yale University, New Haven, Conn.

[21] Appl. No.: 5,470

[22] Filed: Jan. 20, 1987

Related U.S. Application Data

[63] Continuation-in-part of Ser. No. 777,233, Sep. 18, 1985, abandoned.

[51] Int. Cl.$^4$ .............. C12Q 1/68; C07H 21/00; C12N 15/00
[52] U.S. Cl. .............................. 435/6; 435/803; 435/810; 435/172.3; 935/78; 935/28; 536/27; 436/808
[58] Field of Search ............... 435/6, 803, 810, 172.3; 436/501, 530, 808; 536/27; 935/28, 78; 530/367; 548/303

[56] References Cited

U.S. PATENT DOCUMENTS 4,358,535 11/1982 Falkow et al. .................. 435/34 X
4,395,486 7/1983 Wilson et al. .................. 436/508 X

OTHER PUBLICATIONS

Bryant, F. R. et al, *Proc. Natl. Acad. Sci. USA*, vol. 82, 1985, pp. 297–301.
Flory, J. et al, *Proc. Natl. Acad. Sci. USA*, vol. 81, 1984, pp. 7026–7030.
Riddles, P. W. et al, *J. Biol. Chem.*, vol. 260, 1985, pp. 170–173.

*Primary Examiner*—Johnnie R. Brown
*Assistant Examiner*—Jeremy M. Jay
*Attorney, Agent, or Firm*—Peter J. Dehlinger

[57] ABSTRACT

A stable, single-stranded nucleoprotein filament adapted to complex specifically and stably with a target duplex DNA having a selected base sequence. The filament is composed of a single-stranded DNA probe having a region of homology with the target base sequence, and RecA protein bound stably to the DNA probe by adenosine 5'-(γ-thio)triphosphate. The filament is useful in a novel system and method for enriching target duplex DNA which contains a region homologous to the probe sequence, for blocking selected restriction endonuclease sites in the target DNA, and in other DNA methodologies in which stable rapid triple-strand synaptic formation in duplex DNA can be exploited.

14 Claims, 3 Drawing Sheets

RECA NUCLEOPROTEIN FILAMENT AND METHODS

This invention was made with Government support under Grant Numbers GM 33504 and GM 32156 awarded by the National Institutes of Health. The Government has certain rights in this invention.

This application is a continuation-in-part of U.S. application Ser. No. 777,233, filed Sept. 18, 1985 now abandoned.

FIELD OF THE INVENTION

The present invention relates to RecA filaments for complexing with homologous target duplex DNA, and to methods employing the filament to produce homologous, triple-strand complexes.

REFERENCES

Brigati, D. J., et al., Virology 126: 32 (1983).
Church, G. M., and Gilbert, W., Proc Natl Acad Sci USA 81: 1991 (1984).
Cox, M. M., et al., J Biol Chem 256(9): 4676 (1981).
Cox, M. M., et al., Proc Natl Acad Sci USA 78: 3433 (1981).
DasGupta, C., et al., Cell 25: 507 (1981).
Derynck, R. et al., Cell 38: 287 (1984).
Doefler, W., Ann Rev Biochem 52: 93 (1983).
Herman, T., et al., Anal Biochem 156: 48 (1986).
Honigberg, S. M., et al., J Biol Chem 260: 11845 (1985).
Keener, S. L., J Bacteriol 160: 153 (1984).
Kenne, K., et al., Nuc Acid Res 12: 3057 (1984).
Kmiec, E., Cold Spring Harbor Symp, 48: 675 (1984).
Leary, J. J., et al., Proc Natl Acad Sci (USA) 80: 4045 (1983).
Lovett, C. M., J Biol Chem 260: 3305 (1985).
McEntee, K., et al., Proc Natl Acad Sci USA 77: 857 (1980).
Maniatis, T., et al., "Molecular Cloning: A Laboratory Manual", Cold Spring Harbor Laboratory (Cold Spring Habor, N.Y.) (1982)
Pierre, A., et al., J. Biol Chem 258: 2870 (1983). *Previews*, published by Pierce Chemical Co., Rockford, IL, December (1984).
Radding, C. M., Ann Rev Genet 16: 405 (1982).
Radding, C. M., et al., J Mol Biol 116: 825 (1977
Riddles, P. W., et al., J. Biol Chem 260: 170 (1985).
Shibata, T., et al., J Biol Chem 257: 370 (1982).
Shibata, T., et al., Methods in Enz 100: 197 (1983).
Welcher, A., et al., Nuc Acids Res, submitted.
West, S., et al., J Biol Chem 258: 4648 (1983). cl BACKGROUND OF THE INVENTION RecA or RecA-like protein (RecA) is present in many bacteria (Radding, 1982, Pierre, Lovett, West, Keener) and eukaryotes (Kmiec, Keene). The protein functions, in part, to promote homologous pairing of a single-strand DNA with duplex DNA. The pairing reaction appears to involve three distinct phases (Radding, 1982): (1) A slow presynaptic phase consists of the polymerization of RecA on single-strand DNA. The presynaptic reaction depends on ATP, and, in fact, RecA is known to have single-strand DNA-dependent ATPase activity; (2) A rapid synaptic phase can be subdivided into two sequential steps—conjunction, which involves the coming together of single- and double-stranded DNA that is mediated by RecA, independent of homology, and homologous alignment, resulting in synaptic triple-strand complexes between the presynaptic single-strand elements and homologous portions of the duplex DNA. (3) A slow postsynaptic phase of strand exchange results in heteroduplex DNA and displacement of an old strand from the duplex DNA.

Heretofore, it has been shown that ATPγS, the non-hydrolyzable γ-thiol analog of ATP, specifically blocks strand exchange (postsynapsis), but that RecA protein can make joint molecules (synaptic complexes) to a limited extent in the presence of the analog, if *E. coli* single-strand binding protein (SSB) is present (McEntee, Cox, Riddles). In the studies reported, SSB was required for complex formation, and it was necessary to add RecA last to a preincubated mixture of single-strand DNA, duplex DNA, SSB, and ATPγS, in order to achieve homology-dependent complex formation. If the duplex DNA was added last, complex formation was independent of homology between the single-strand and duplex DNA species. Under the best conditions (adding RecA last), the extent of homologous complex formation produced was only about 5% of the total possible complex formation (Riddles)

SUMMARY OF THE INVENTION

The invention includes, in one aspect, a stable, single-stranded nucleoprotein filament effective to complex specifically and stably with a target duplex DNA having a selected base sequence, in the absence of single-strand binding protein. The filament includes a single-stranded DNA probe having a region of homology with the selected target base sequence, and RecA protein molecules bound stably to the DNA probe in the presence of adenosine 5'-(γ-thiol)triphosphate.

In one embodiment, the RecA is bound to the probe at a preferred $Mg^{++}$ concentration of between about 0.5–2 mM, to a final RecA concentration of about 1 RecA molecule per 3–6 probe nucleotides. In another embodiment, designed particularly for use in complexing with circular target DNA, the probe is formed in the presence of up to 10–20 mM $Mg^{++}$, at an optimal RecA concentration which is determined by the total amount of DNA in a reaction mixture containing the filament and target DNA.

The probe may also include ligand molecules derivatized to the probe nucleotides, for use in binding the filament and attached target duplex DNA selectively to a solid support. The probe preferably includes biotin molecules which are linked to the nucleotides through disulfide bonds, and/or are complexed with avidin, streptavidin, or an analog thereof, for binding to a solid support through a copper chelate complex.

The filament is useful in a novel DNA-purification system described below, and has other uses in selectively blocking restriction site cleavage within the region of homology in a triple-strand complex. This feature can be used for restriction fragment analysis, to determine relationships between a DNA probe (in the filament) and target restriction fragments. The analysis is performed by complexing the filament to genomic DNA fragments of interest, digesting the fragments with one or more selected restriction endonucleases, and analyzing the pattern of digest fragments by electrophoretic separation.

The ability of the filament to block restriction cutting at a selected duplex site can also be exploited in vector cloning manipulations. In this application, the filament is designed to complex selectively with a region containing a selected restriction site, to protect the site against cleavage by the corresponding restriction enzyme.

The system of the invention is designed for separating target and non-target duplex DNA molecules on the basis of a selected base sequence which is unique to the target sequence. The system comprises the above single-stranded nucleoprotein filaments, and a solid support designed to selectively bind target duplex DNA molecules which are complexed with said filaments by homologous alignment.

In one embodiment, the solid support is a glass-fiber filter effective to selectively bind target DNA containing D-loops which are characteristic of homologous filament/target complexes. In another embodiment, the solid support has surface-bound avidin, streptavidin, or an analog thereof, for selectively binding target molecules complexed with biotinylated filaments. A third embodiment includes a solid support derivatized with iminodiacetic acid moieties, for binding selectively, in the presence of $Cu^{++}$, to target molecules complexed with filaments containing derivatized biotin and attached avidin, streptavidin, or analogue thereof.

The system of the invention is used in a novel method for separating target and non-target duplex DNA molecules on the basis of a selected base sequence which is unique to the target sequence. In practicing the method, filaments of the type described above are reacted with the target and non-target DNA molecules under conditions which promote rapid homologous alignment between the probe and homologous target base sequences in the reaction mixture, with formation of a stable filament/target complex. The complex is contacted with the above solid support, to selectively bind target molecules which are complexed with the filaments by homologous alignment. After washing the support to remove non-bound material, the support is treated to release target DNA.

The method has been applied to both linear and circular target duplex DNA. One preferred method for separating linear DNA involves trapping the filament/target complex selectively on a glass-fiber filter. The procedure, which gives high recovery of target DNA, can be repeated through two or more rounds to give high purification of target material originally present at a ratio of 1:000 or less in a DNA duplex mixture.

One preferred method for separating circular target DNA, such as plasmid DNA, involves binding the filament/probe complex, by means of biotin/avidin binding or copper-mediated avidin/iminodiacetic acid binding to a solid support, and releasing the target DNA after removal of non-target material. The method routinely gives $10^4$ to $10^5$ fold enrichment in target sequences, with a yield typically between about 10-20 percent. The separated target sequences can be further purified by propagation in a bacterial host, and further screening by colony hybridization methods.

These and other objects and features of the invention will become more fully apparent when the following detailed description of the invention is read in conjunction with the accompanying drawings.

DETAILED DESCRIPTION OF THE INVENTION

I. Reaction Components

A. Single-Stranded DNA Probe

Figure 1:
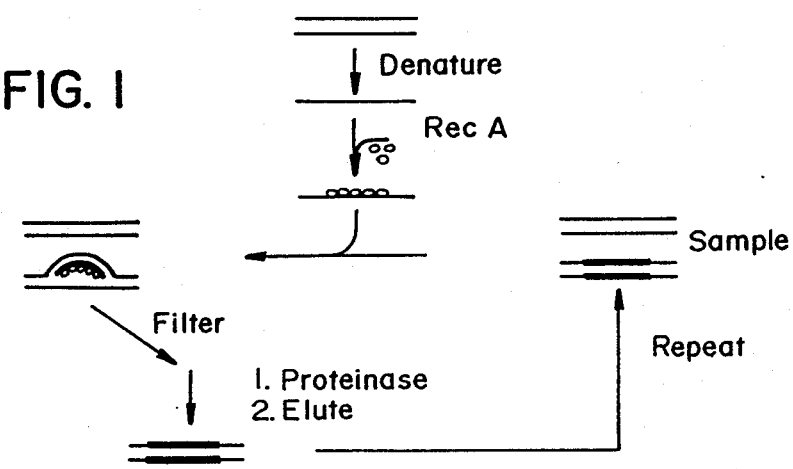
FIG. 1 illustrates steps used in enriching a DNA duplex fragment by differential target binding to a glass-fiber filter, according to one embodiment of the invention.

The nucleoprotein filament of the invention contains a single-strand DNA probe having a region of homology with a selected base sequence in a target duplex DNA. As the term is used herein, probe "homology" with the target means that the single-strand probe and target duplex have a region of similar or exact base pair sequence which allows the probe, with such functionally complexed with RecA, to recognize and complex specifically with the corresponding base pair region in the duplex target. The extent of base pair mismatching which is allowed without losing homology may be as high as 20%-30%, depending on the distribution and lengths of mismatched base pairs.

The length of required homology between probe and target is at least about 20-200 base pairs, although certain rate and stability limitations may be encountered with homologous regions in this size range, as will be discussed below. Preferably, the probe has a region of homology of at least about 500 base pairs, and typically, up to several kilobases. According to one advantage of the invention, the probe nucleoprotein filament forms a stable complex with target duplex either with or without nonhomologous probe end regions. Therefore, the probe may include only regions of homology with the target DNA, or may include a homologous segment flanked at one or both ends by nonhomologous segments.

The probe DNA is derived typically from a duplex cloning vector, such as a plasmid, phage, or cosmid vector, which contains a region of homology with the target DNA. For many target regions of interest, cloned genomic or cDNA fragments are available. Where a cloning vector with a suitable region of target homology is not available, a probe fragment, such as a genomic or cDNA fragment may be placed in a cloning vector and the probe-containing vector identified and isolated by well-known methods (reference 11).

To obtain the cloned probe, a cloning vector containing the probe is digested with selected restriction enzyme(s), to form one or more linear vector fragments. For larger vectors, the digest fragments are preferably fractionated to yield one or more probe-containing fragments in purified form, although a mixture of homologous and nonhomologous fragments can be tolerated.

For applications involving very short regions of homology, the DNA probe may be prepared conveniently as a single-strand synthetic oligonucleotide. For example, if the nucleoprotein filament formed from the probe is designed to complex with and block a single restriction site in a cloning vector, where the base sequence of only a short segment containing the restriction site is known, an oligonucleotide complementary to the known sequence would be suitable. Oligonucleotides are readily prepared by well-known synthetic methods. Section II considers reaction conditions which favor binding of small nucleoprotein filaments to target DNA.

B. Labeled Probes

In a variety of applications discussed below, the probe is labeled with radioactive nucleotides, and/or with ligand molecules which can be used in binding the filament, with attached target dsDNA, to a solid support. In the usual case, the probe is labeled in double strand form, then denatured and isolated in single strand form for use in the RecA reaction which leads to the probe/target complex.

Radiolabeling DNA can be done by a variety of known methods, including nick translation and end labeling of double strand DNA (Maniatis) or by incorporation of radiolabeled nucleotides into synthetic probes. The methods outlined in Example VII are generally adaptable to radiolabeling of dsDNA.

The ligand molecules used for labeling the probe are characterized by high affinity binding with binding molecules which can be attached to a solid support. That is, the binding molecules are capable of recognizing and binding with high affinity to ligands carried on the probe. The ligand may be any molecule which (a) can be attached to the probe polynucleotide, (b) does not interfere with formation of probe/RecA filaments, (c) allows homologous alignment of the filament with double-strand DNA, and (d) can be recognized and bound by molecules carried on a solid support, when the probe is complexed with the target.

One general class of ligands includes haptens or antigens which are immunoreactive with high affinity to anti-ligand antibodies (the binding molecules in the system). One preferred ligand is biotin which can be readily derivatized to nucleotides, and which binds specifically and with high affinity to avidin, streptavidin, and analogues thereof carried on a solid support. As will be seen below, the biotin can be derivatized to probe nucleotides, through relatively long linker arms, without loss of ability of the probe to hybridize with ds target DNA in a RecA-mediated reaction.

Another preferred ligand is the biotin/avidin complex formed when a biotinylated probe is mixed with avidin, streptavidin, or analog thereof. The avidin in the biotin/avidin complex is capable to binding with high affinity to chelator groups, such as iminodiacetic acid, carried on a solid support, through formation of an avidin/$Cu^{++}$/chelator complex (Welcher). The advantage of this system is that (a) the probe can be reacted with RecA, and subsequently with ds target DNA before addition of avidin, and (b) the avidin chelate complex can be disrupted readily, by addition of a soluble chelator, such as EDTA, to release the probe/target complex from the column.

Two preferred biotin-labelled nucleotides for use in preparing biotinylated probes are Bio-11-dUTP (Brigati), which has an 11-atom linker arm separating the the biotin and pyrimidine base, and Bio-19-SS-dUTP (Herman), in which the biotin and base are separated by a 19-atom linker containing a disulfide bond. The latter probe is particularly useful in a system which involves binding of a biotinylated probe to avidin solid support, since the probe can be readily released from the support by a mild reducing agent, such as dithiothreitol, capable of cleaving the linker disulfide bond (Herman).

Methods for incorporating biotinylated dATP or dUTP into ds DNA have been described (Leary, Brigati, Welcher). The incorporation methods generally follow procedures for incorporating radiolabeled nucleotides into dsDNA by nick-translation or end labeling, such as detailed in Example VII. In general, nick translation is preferred for biotinylating probes longer than about 1 kbase, and end labeling is preferred for shorter probes. End-labelling is also preferred where the target dsDNA which is purified by the solid support method is to be used subsequently for transforming bacteria. Experiments conducted in support of the present invention show that when the probe is uniformly biotinylated by nick-translation with Bio-11-dUTP (bearing a noncleavable linker) and the probe/target complex is purified by cupric-iminodiacetic acid chromatography, no transformable homologous plasmid is recovered. Apparently, the several biotins spaced at intervals along the probe bind several avidin molecules irreversibly or one avidin binds more than biotin, thereby "locking" the plasmid-probe-biotin-avidin complex and producing a topologically unreleasable plasmid. Release of a nick-translated probe-plasmid complex from avidin by reduction of the disulfide bond of Bio-19-SS-dUTP gave variable results and was not pursued rigorously. In contrast, when the probe is end-biotinylated (as in Example IX), the target plasmid is released efficiently from the probe and produces *E. coli* transformants.

C. RecA Protein

The RecA is preferably obtained from *E. coli*, although RecA or RecA-like proteins are present in a variety of other organisms. RecA or RecA-like proteins have been identified in *Salmonella typhimurium* (Pierre), *B. subtilis* (Lovett), *Proteus mirabilis* (West) and other bacteria, including *Proteus vulgaris* (Keener). A fungal source of a recombination protein is reported in the Kmiec reference and the Keene reference describes a RecA-like protein from humans. Methods for obtaining RecA from *E. coli* at high purity and good yields have been published (Shibita, Cox). The protein is available commercially from PL Biochemicals (Milwaukee, WI).

D. Double-Strand Target DNA

Studies conducted in support of the invention show that stable synaptic complex formation occurs with both circular and linear target duplex DNA substrates. The circular duplex substrate may be in an unnicked, supercoiled form or in a relaxed form containing a single nick in the region of homology; similarly the linear DNA may be nicked or unnicked, and the region of probe homology may be located either internally or at a free end of the target substrate.

Methods for preparing linear or circular duplex targets are well-known, and the target source and preparation methods will be clear from the particular application, as described in Section IV. In one general application, the target duplex is typically a linear duplex fragment contained in a mixture of fragments, such as genomic, cDNA, or vector digest fragments, which contain a large portion of non-homologous duplex material. In another general application, the target is a circular recombinant plasmid carrying probe sequences of interest, such as sequences of a cDNA library.

II. Probe/Target DNA Complexing: Method 1

A. Filament Formation-Method

In this method, a stable RecA/probe filament is formed by reacting the ss probe with RecA under low $Mg^{++}$ conditions which have been discovered to produce efficient binding of RecA to the probe, at a saturating density of the protein on the probe. Specifically, the DNA probe from above is suspended in a low-salt reaction medium containing between about 0.5 to 2 mM $Mg^{++}$, and 5'-(thio)triphosphate (ATP$\gamma$S), at a preferred concentration of between about 0.5 to 2 mM. The concentration of DNA is preferably between about 0.1–50 $\mu$M, expressed as the molarity of individual nucleotides making up the DNA. The pH of the reaction medium is preferably about 7.5. If the DNA probe is obtained in duplex form, the suspension must first be heated to above the DNA melting temperature, e.g., 100° C., in low salt buffer to denature the duplex material. After heating, the denatured material is rapidly cooled on ice to prevent renaturation.

Studies carried out by the inventors suggest that the efficient RecA binding to single-strand DNA occurs when the single strand probe has diminished secondary structure. The diminished structure can be achieved either by the addition of SSB to the reaction, at a $Mg^{++}$ concentration of greater than about 3 mM, or by reducing $Mg^{++}$ in the reaction medium to between about 0.5 to 2 mM $Mg^{++}$, and preferably 1 mM, with no addition of SSB required. Although $Mg^{++}$ is the most critical cationic species in the reaction mixture, care should be taken to avoid the presence of other cationic species, particularly divalent metal ions, which can effect secondary structure in the DNA. One preferred reaction medium (Example I) is a 31 mM Tris-HCl buffer, pH 7.5, containing 1 mM MgCl, 1.2 mM ATP$\gamma$S, and 0.4 mM dithiothreitol (DTT), a mild reducing agent.

RecA is added to the single-strand DNA suspension to a final mole ratio of no less than about 1 RecA per 4 nucleotides, and preferably at a mole ratio of about 1 Rec A per 3 nucleotides. Thus for a 1 kb probe, the molar ratio of RecA to probe should be at least about 333:1.

After addition of the RecA, the reaction mixture is incubated preferably for about 10 min at 37° C. to form the nucleoprotein filaments, which have a mole ratio of about 1 RecA molecule per 4 nucleotides. Studies performed in support of the invention indicate that filaments having a RecA/nucleotide ratio of between about 1:4 to 1:6 promote optimal formation of joint molecules, and that at a ratio of 1:12, the extent of formation of joint molecules has dropped off sharply. The RecA density for joint formation, which includes at least the range 1:4 to 1:6 RecA molecules per nucleotides, is referred to herein as a functionally saturating amount of RecA.

The nucleoprotein filaments are stable against loss of activity—as measured by the ability to form joint molecules with target DNA—when incubated at 37° C. for up to 10 hr. The nucleoprotein filaments can be stored at refrigerator temperature over a several-day period without appreciable loss of activity. For longer storage periods, the filaments can be frozen or lyophilized. Studies conducted in support of the application show no loss of activity after freezing, even after several weeks.

B. Stable Triple-Strand Complex Formation

When the above ATP$\gamma$S nucleoprotein filament is added to homologous target duplex DNA, the filament rapidly and efficiently complexes with the DNA, forming a stable triple-strand synaptic complexes. To form the synaptic complex, the duplex DNA and nucleoprotein filament are combined in a buffer reaction medium which differs from the reaction medium used for filament formation in that a $Mg^{++}$ concentration of at least about 4 mM is required. The minimum $Mg^{++}$ concentration was determined from binding studies previously reported by the inventors (Honigberg). Efficient complex formation occurs over a $Mg^{++}$ concentration range of between about 4 and 25 mM or higher. The reaction medium used in Example III, containing 12 mM MgCl$_2$, 1.2 mM APT$\gamma$S and 31 mM Tris-HCl, pH 7.5, is generally suitable.

Filament single-strand DNA is added to the target duplex at a mole ratio typically 1:1 to 1000:1, based on the mole ratio of homologous-base nucleotides. It is noted that the molar ratio is calculated on the basis of target duplex DNA, and not total duplex DNA. Thus a 1000:1 molar ratio of filament DNA in a fragment mixture of 0.1% target DNA would include approximately the same quantities of single-strand and duplex DNA. Increasing the filament-to-target ratio will increase the rate of synaptic complex formation and, where the filament DNA is a relatively short single strand segment (less than 200 base pairs), will increase the stability of the complex by a mass action effect.

The final concentration of DNA in the reaction medium is preferably at least about 1 $\mu$g/ml and typically 1–10 $\mu$M or greater. At concentrations lower than about 1 $\mu$M, the rate of complex formation decreases significantly, presumably because of reduced conjunction preceding homologous alignment. The DNA which contributes to the desired DNA concentration may be filament single-strand DNA, duplex target DNA, or heterologous non-target duplex DNA. Thus, addition of heterologous (non-target) duplex DNA to a dilute suspension of target DNA will accelerate the rate of filament/target complex formation, even though the heterologous DNA is not involved in the final complex, assuming that the filament is present in at least equimolar amount to the total ds DNA.

The reaction mixture is incubated at a preferred temperature of 37° C. until the synaptic reaction has gone to completion. The progress of the reaction can be followed by assaying the formation of joint (synaptic) molecules, based on D-loop-specific binding to nitrocellulose filters (DasGupta). Typically, the filament or target DNA is radiolabeled, and the filters counted for bound radioactivity by conventional methods. A reaction time of 15–30 min is usually adequate for filaments with homologous regions of about 500 base pairs or greater. For smaller filament DNA sizes, longer reaction times are required.

The ATP$\gamma$S synaptic complex can be trapped efficiently on nitrocellulose filters, but the recovery of products from these filaments is low. It has been discovered, however, that the ATP$\gamma$S synaptic complex binds efficiently to glass fiber filters (unlike the analogous ATP complex) and can be recovered in good yield to eluting the complex after treatment with a filament-dissociating agent, such as protease, as described in Section IV. This allows the ATP$\gamma$S complex to be purified readily by filter trapping and elution, according to the scheme outlined in FIG. 1. Alternatively, the complex may be separated from non-complexed DNA by affinity binding of a ligand-labeled probe to a solid support, according to procedures outlined generally in FIG. 2. Both DNA separation schemes will be detailed below in Section IV.

III. Probe/Target DNA Complexing: Method 2

According to another aspect of the invention, it has been discovered that sequence-specific probe/RecA/ds target DNA complexes can be formed efficiently by carrying out both the filament-forming reaction and the subsequent filament/target complexing reaction at a moderate $Mg^{++}$ concentration, e.g., between about 5–15 mM $Mg^{++}$.

Figure 3:
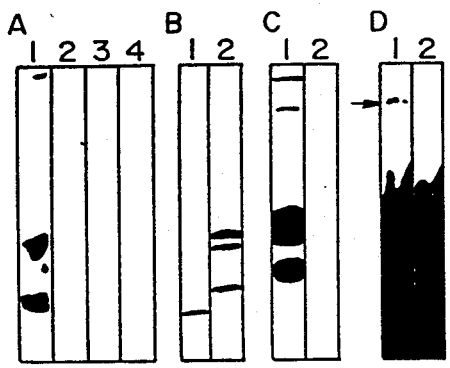
FIG. 3 shows gel electrophoresis patterns of A: pBR322 plasmid complexed with nick translated radiolabeled pBR322 probe/RecA filament (lane 1), probe/RecA filament alone (lane 2), pBR322 plasmid and nick-translated radiolabeled pBR322 probe in the absence of RecA (lane 3), and heterologous double stranded M13 derivative ("M13") DNA and nick translated radiolabeled pBR322 probe/RecA filament (lane 4); B: different topological forms of pBR322 plasmid (lane 1) and M13 (lane 2); C: pBR322 plasmid complexed with nick translated, radiolabeled, biotinylated pBR322 probe/RecA filament (lane 1), and probe filament alone (lane 2); and D: a recombinant cosmid complexed with nick translated, radiolabeled, biotinylated 6.5 kb probe having a region of homology with the cosmid (lane 1, arrow), and probe alone (lane 2)
Figure 4:
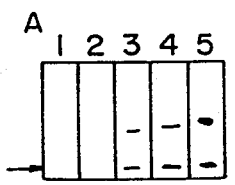
FIG. 4 shows gel electrophoresis patterns of A: pBR322 plasmid complexed with nick translated radiolabeled, biotinylated pBR322 probe/RecA filament formed at concentrations of pBR322 plasmids ranging from 0.0032 nM (lane 1) to 0.32 nM (lane 6); B: same as A, but with increasing concentrations of RecA, ranging from 0.08 μM (lane 1) to 5.12 μM; C: same as A and B, but increasing concentrations of probe, ranging from )0.14 fmoles (lane 1) to 7.2 f moles (lane 6); and D: complex which has formed at increasing time intervals from 1 minute (lane 1) to 10 minutes (lane 5) after addition of target pBR322 to the probe/RecA filament.

The target specificity, reaction requirements, and effects of different reactant concentrations have been examined, and are reported in part in Example VI, with reference to FIGS. 3 and 4. Generally these studies were carried out by first forming RecA/probe filaments by reacting ss probe, incorporating either radiolabeled nucleotides and/or biotinylated nucleotides, with RecA, in the presence of 8 mM $Mg^{++}$, 2 mM $CoCl_2$, and 1.6 mM ATP$\gamma$S. After 10 min incubation at 37° C., homologous and/or heterologous ds DNA was added, at the same magnesium, cobalt and ATP$\gamma$S concentrations, and reacted further for 10 minutes, to form probe/RecA/target duplex complexes. The reaction mixture was then treated with proteinase K and sodium dodecyl sulfate (SDS), to remove RecA, and fractionated by gel electrophoresis. Here it is noted that the stability of the complex, after removal of the RecA protein, is due in part to the superhelical form of the circular DNA target.

The gels shown in FIG. 3 are of reaction complexes formed with radiolabeled probes (3A), biotinylated probes (3C) and cosmid target DNA (3D). As discussed in detail in Example VI, the gel results indicate that (a) probe complex formation with dsDNA in the presence of RecA is specific for homologous target dsDNA, and requires RecA, (b) complex formation occurs with different topological conformations of the target, and complex formation with biotinylated probe appears to be as efficient as with "native" ss DNA.

FIGS. 4A–4C show the extent of complex formation (indicated by the arrow in the figures) at varying concentrations of (A) ds target DNA, (B) RecA, and (C) ss probe. In all of the reactions, the concentrations of $Mg^{++}$, $Co^{++}$, and ATP$\gamma$S are as above. The concentration of ds target DNA in the first series of experiments ranged from 0.0032 nM (lane 1 in 4A) to 0.32 nM (lane 5 in 4A). Complex was first observed at a target concentration of 0.032 nM and visibly increased at higher target concentrations.

According to an important feature of the method, it has been discovered that the extent of complex formation is biphasic with respect to RecA concentration, and that the optimal concentration of RecA is dependent on the total amount of DNA (including probe and ds species) contained in the final reaction mix. The biphasic response to RecA concentration is shown in the series of experiments described with respect to FIG. 4B. Here increasing amounts of RecA protein, ranging from 0.08 $\mu$M (land 1) to 5.12 $\mu$M (lane 7), were added to reaction mixtures containing fixed amounts of the probe and homologous target duplex DNA. As seen, optimal complex formation (for the given amounts of probe and target DNA present) occurs at an RecA concentration of about 0.32 $\mu$M, and is dramatically reduced below about 0.16 $\mu$M. and above about 0.64 $\mu$M RecA. Other experiments performed in support of the invention, but not detailed here, indicate that the optimal concentration of RecA in the complex-formation reaction increases with increasing concentration of total DNA in the reaction mixture. Thus, in any reaction system, it is important first to establish, for the particular ss probe and ds DNA concentrations used, a concentration of RecA that produces optimal or near-optimal probe/RecA/target dsDNA complex formation.

It is noted here that at the optimal concentration of RecA in the above series of reactions, the mole ratio of RecA to probe is 0.32 $\mu$M:8 fmole (per 100 $\mu$l) or about 700:1. Assuming a probe size of about 1 kb, this gives a RecA:probe nucleotide ratio of about 0.7:1, or about 2–3 fold higher than the optimal RecA:probe nucleotide ratio of about 1:4 noted for the method of Section II.

THe inventors have proposed two possible reasons for the different RecA concentrations requirements in the two methods: The first method may produce more stable RecA association with the probe, and therefore the amount of RecA required to maintain the probe in a "saturated" state is less. Secondly, preliminary evidence suggests that circular superhelical DNA, which has a known ability to unwind transiently among its length, may itself bind RecA and would thus draw RecA out of solution and possibly even off the probe. This latter explanation is consistent with the finding herein that the optimal RecA concentration is dependent on the total ss and ds circular DNA in the reaction mixture.

A third series of tests, reported with respect to FIG. 4C, shows the effects of increasing probe concentrations, at fixed concentrations of RecA and target ds DNA. Probe concentrations ranged from 0.71 fmoles (lane 1) to 5.12 fmoles (lane 6). The gel patterns show that increasing the ratio of probe:target increases the amount of probe/target complex formed, up to a probe:target DNA mole ratio of about 1:1 (lane 4), as anticipated.

FIG. 4D shows gel patterns of complex formed as above after incubation periods ranging from 1 minute (lane 1) to 10 minutes (lane 5). No difference in gel patterns was observed over time, indicating that the reaction was substantially complete after 1 minute.

IV. Purification of Probe/Target DNA Complexes

The invention provides a rapid and efficient method for enriching or purifying a target DNA fragment containing a region of homology with the filament probe DNA. Typically, the target fragments are part of a gene fragment mixture in which the proportion of homologous DNA may be quite small, on the order of 0.1% or less. The DNA mixture containing a homologous fragment to be enriched can include gene banks of genomic or cDNA libraries prepared in recombinant DNA cloning vectors, such as conventional cosmid cloning vectors (Maniatis); and restriction digests of DNAs isolated from tissues, cell lines, or whole organisms, i.e., genomic digests.

A. Unlabeled Probe/Target Complexes

Figure 2:
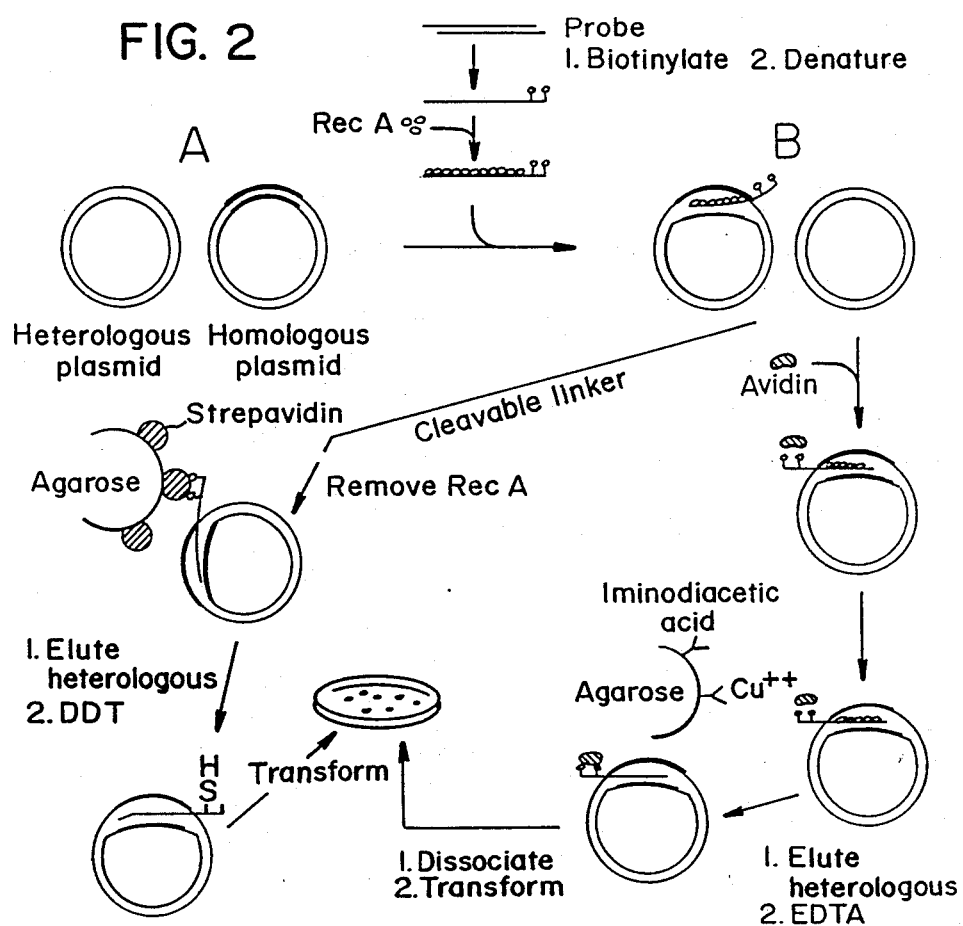
FIG. 2 illustrates steps used in enriching a DNA duplex fragment by streptavidin chromatography (A) and iminoacetic acid chromatography (B) according to another general embodiment of the invention.

According to one aspect of the invention, it has been found that the probe/RecA/target duplex complex formed by the complex-formation methods discussed above can be fractionated from non-complexed DNA on the basis of selective binding of the complex to a glass-fiber filter. The DNA separation steps in this method are illustrated in FIG. 1, which shows the steps of producing a RecA/probe filment, by denaturing a ds probe species and reaction with RecA, and reaction of the RecA filament with a mixture of linear ds DNA fragments, one of which contains a region of homology (indicated by broadened line) with the probe. The filament and probe/target complex can be formed by either of the two methods above. The complex is shown in the figure with a characteristic D-loop structure.

The synaptic complex mixture is passed through a glass fiber filter, such as a Whatman GF/C filter, which efficiently traps D-loop structures, but not ordinary duplex fragments. The filter is washed to thoroughly remove nonhomologous duplex DNA, then treated with proteinase K to release RecA and the probe from the complex, and allow elution of the ds target species from the filter. The separation procedure is illustrated in Example IV, which shows an approximately 64-fold enrichment in a DNA mixture in which the homologous target sequence is initially 1 percent of total fragment DNA, and in Example V, which shows about a 35-fold enrichment of a 0.1% fragment mixture.

The filter elution procedure can be repeated one or more times if additional enrichment of the homologous fragment is desired. Alternatively, the enriched material may be further purified by the following affinity separation procedure.

B. Ligand-Labeled Probe/Target Complexes

This separation procedure uses a DNA probe having one or more bound ligands, such as biotin, by which the filament/duplex complex can be captured by binding molecules carried on a solid support. The general method will be described and illustrated herein for a separation system having a biotinylated probe, for probe/target binding to a solid support designed to bind specifically to biotin or to a biotin/avidin complex. It will be understood that the general procedures described can be adapted readily to systems containing other ligand/binding molecule pairs, such as antigen/antibody pairs.

The system and method involving binding of a biotinylated probe to an avidin solid support is illustrated in FIG. 2A. The steps of providing a ss biotinylated probe, forming a probe/RecA filament, and reacting the filament with a mixture of homologous and heterologous ds DNA, as indicated, have been described above. Also as indicated in the figure, the biotin ligands are linked to the probe through a cleavable linker, such as a disulfide bond, which allows the complex to be released readily from the avidin column by washing with a suitable cleaving agent.

The solid support used for separating the probe/target complex is preferably a suitable column chromatography support material, such as agarose, which has covalently attached avidin, streptavidin, or analog thereof. Streptavidin and avidin-DN (Example IX) are preferred because these binding molecules have no net charge and thus show less non-specific ionic interaction with polynucleotides. The commercially available streptavidin/agarose column material used in Example VIII is suitable.

Before column separation, the reaction mixture may be treated to release RecA protein from the probe/RecA/target DNA complex. Releasing the RecA reduces non-specific binding interaction with the solid support, and may also reduce the possibility of RecA interference with probe binding to the support by steric effects. The RecA can be released by treatment with proteinase K and SDS, as described in Example VIII.

The material is then applied to the column, which is washed extensively to remove non-specifically bound material, then eluted with a suitable elution buffer. In the preferred embodiment, where the probe contains a cleavable bond, such as a disulfide bond, the elution buffer of course contains a cleaving agent, such as dithiothreitol (DTT), effective to release the probe from the support by breaking such bonds.

Figure 5:
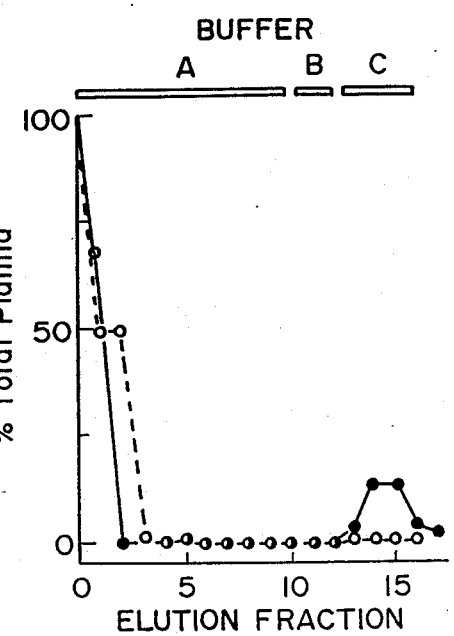
FIG. 5 shows the elution profile of radiolabeled plasmid DNA reacted with biotinylated RecA probe which is either homologous (open circles) or heterologous (closed circles) to the probe, as separated by a streptavidin-column chromatography.

The eluted material may be assayed for target enrichment by a variety of techniques capable of distinguishing homologous (target) DNA from heterologous DNA contained in the original DNA sample. In the method described in Example VIII, homologous DNA is assayed by blotting the material on a nitrocellulose filter, and hydridizing the material with a radiolabeled probe. The results of the assay, shown in FIG. 5 and discussed in Example VIII, indicate a substantial separation of the homologous DNA (solid circles in FIG. 5), with a recovery in the eluted separation fractions 13–16, of about one-third of the original material.

In the case where the target DNA is contained by a suitable cloning vector, such as a fragment of genomic DNA in a cosmid vector, the target may be further purified, as indicated at the bottom of FIG. 2A, by transforming a suitable bacterial host with the separated target material (contained in a vector), and selecting for bacterial colonies which contain the target sequence. The latter selecting can be accomplished by conventional techniques, such as probe hybridization, or colony selection, where the target-containing vector carries a selectable marker not carried in the heterologous material.

The second general method for DNA separation, based on affinity chromatography with a biotinylated probe, is illustrated in FIG. 2B. In this procedure, the reaction mixture contains probe/RecA/target complex is first reacted with avidin (or analogue thereof) to bind avidin to the complex, as shown. Preferably streptavidin, or avidin-DN, both characterized as having no net charge, are used in the method. It is noted here that the reaction mixture is not treated, for example, with proteinase K and SDS, to release RecA as in the method above, since such treatment with also disrupt the avidin (or analog) bound thereto.

The solid support used in the method has surface-bound chelating groups, such as iminodiacetic acid groups, capable of forming $Cu^{++}$ chelate complexes with avidin. The commercially available inimodiacetic acid-agarose support used in Example IX is suitable.

The material is applied to the solid support, typically on a column, washed extensively to remove heterologous DNA in the mixture, and then eluted with a chelating agent, such as ethylenediaminetetraacetic acid, having a high binding affinity for cupric copper. The chelator thus acts to disrupt the avidin/support attachment by removal of the copper involved in the binding chelation complex. The column chromatography techniques described generally in Example IX are applicable.

Figure 6:
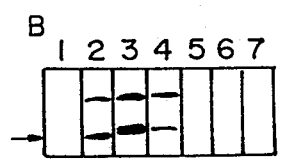
FIG. 6 is a plot of the ratios of homologous/heterologous plasmids, as determined by the number of bacteria transformed by each of the two plasmids, after separation of the plasmids in the presence of a biotinylated, radiolabeled probe/Rec filaments, and separated by iminodiacetic acid chromatography.
Figure 6:
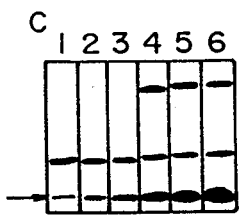
Figure 6:
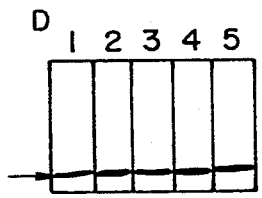
Figure 6:
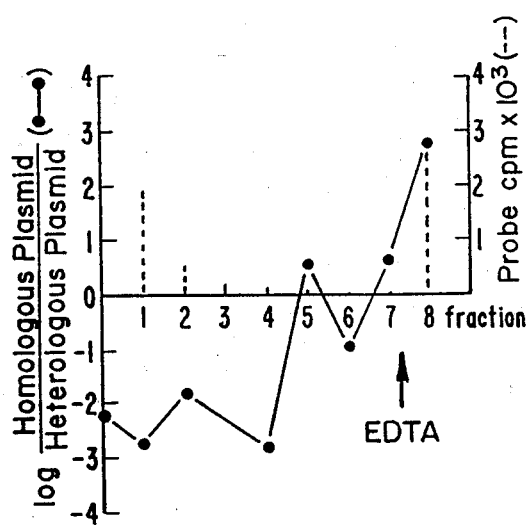

The heterologous and homologous DNA material studied in Example IX are plasmid vectors containing different antibiotic-resistance selectable markers. Thus the degree of separation between the two vectors achieved in the method could be assessed by examining the relative proportions of bacterial host cells transformed with different eluate fraction from the column. The results are shown in FIG. 6, which is a plot of the log of the ratio of homologous to heterologous transformants in the eight eluate fractions from the column. As discussed in Example IX, the data indicate an enrichment in homologous DNA by a factor of about $10^{4.6}$.

V. Applications

A. DNA enrichment

The DNA separation methods described above illustrate the system and method of the invention for enriching duplex DNA having a selected target sequence. Briefly, the system includes a stable, single-stranded nucleoprotein filaments, each composed of a single-stranded DNA probe having a region of homology with the selected base sequence, and RecA protein molecules bound stable to the DNA probe, in the presence of adenosine 5'-(γ-thio)triphosphate, to promote rapid homologous alignment between the probe and homologous target base sequences, with formation of a stable filament/target complex. These filaments are bound to a solid support designed to selectively bind target molecules which are complexed with said filaments by homologous alignment.

The method includes the steps of providing stable, single-stranded nucleoprotein filaments, each composed of a single-stranded DNA probe having a region of homology with the selected base sequence, and RecA protein molecules bound stably to the DNA probe, in the presence of adenosine 5'-(γ-thio)triphosphate, and reacting the filaments with the target and non-target DNA molecules under conditions which promote rapid homologous alignment between the probe and homologous target base sequences in the reaction mixture, with formation of a stable filament/target complex. The reaction mixture is contacted with a solid support designed to selectively bind target molecules which are complexed with said filaments by such homologous alignment. After removing non-bound DNA molecules from the support, the support is treated to release target DNA molecules which are selectively bound to the support through such complex formation.

Considering specific applications of the fragment enrichment procedure, a selected gene can be recovered in enriched form from any of the sources mentioned above. The enriched DNA fragments can then be cloned into a plasmid, virus, cosmid, or lambda bacteriophage vector. The enriched fraction can be further purified, by one or more additional passes, or by using the separated DNA to transform bacteria at a low density, and selecting transformed cells containing the transforming vector of interest.

The enrichment procedure can also be used to facilitate gene walking for distances of several hundred kilobases along portions of a chromosome that flank a region homologous to a given probe. Gene walking provides information about the positions, arrangement, and base sequences of genes over extended chromosome regions and is useful, for example, for genetic analysis of families or populations with regard either to disease states or normal markers.

The fragment enrichment method facilitates gene walking by enriching a whole genomic digest for fragments containing regions of homology with a probe of interest. The enriched fragments will include those having chromosome regions extending up to several hundred kilobases on either side of the selected probe region. The isolated synaptic complex material, which is now enriched for the linked flanking sequences, is disgested by restriction endonucleases and subcloned in a comsid library. Individual clones from this library are then analyzed by making minilysates, followed by digestion with several restriction endonucleases. The fragments are end labeled and analyzed according to size by agarose gel electrophoresis. This analysis will reveal clones that share fragments of identical size, and thus establish a linkage of two clones to each other. Continued extension of this analysis will reveal overlapping sets of cosmid clones that span hundreds of kilobases on either side of the original probe.

The advantage of this approach over existing methods resides in the initial enrichment by the RecA-pairing method of large pieces of DNA in double-strand form that contain DNA homologous to the probe. This eliminates multiple cycles of subcloning and Southern blotting required by existing methods.

Considering a third application of the fragment-enrichment procedure, evidence exists that base modification (methylation for example) is related to the developmental state of the cell (Doefler), and a technique for identifying the location of 5-methylcytosine residues in genomic DNA has been reported (Church). Further, methods for modifying DNA within cells by chemical methylation have been developed, allowing mapping of sites at which DNA is protected by tightly bound proteins. This mapping has been accomplished heretofore by performing chemical sequencing reactions on total DNA followed by blotting and hybridization to a highly labeled probe to analyze.

The fragment enrichment technique makes it possible to enrich cellular DNA for the sequences of interest at a level at which conventional labeling of restriction fragments, by use of polynucleotide kinase, followed by gel purification of the fragments will yield DNA of sufficient purity so that direct sequencing methods can be applied. The sequence can then be determined on the basis of the radioactivity introduced into the original fragments.

The general fragment-enriched method has a number of advantages over conventional hybridization methods. The most impressive advantage of the procedure is that the rate of formation of the synaptic complex is about 10 to 100 times faster than thermal hybridization. Secondly, the target DNA does not have to be denatured, thereby saving time and manipulations and also allowing one to purify and reclone target DNA after purification, something that is currently not practical using the conventional hybridization techniques. Also, undesired side reactions involving intrastrand and interstrand cross-linking between repeated sequences are avoided, since the target is maintained in duplex form.

B. Restriction Fragment Analysis

The uses of restriction fragment analysis generally fall into two categories. The first of these is for analysis of genetic loci found in DNA purified directly from the cell or organism. The second general area of use is for characterization of DNA that has been amplified using vectors commonly used in recombinant DNA procedures. This section explores uses of the duplex-complexing reaction for restriction fragment analysis.

Figure 7A:
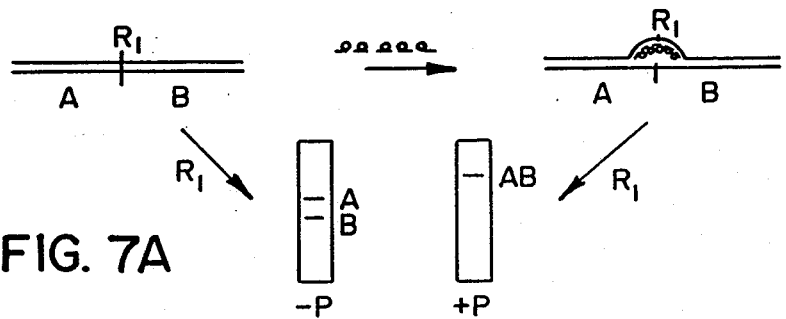
FIGS. 7A and 7B illustrate different applications of the invention for use in restriction fragment analysis.

FIG. 7A illustrates an approach in which a selected restriction site $R_1$ in a fragment A-B is selectively blocked. In this approach, the $R_1$ site is within the region of homology of a probe P which forms the single-strand DNA of a nucleoprotein complex formed according to the invention. When the probe is reacted with the A-B fragment, the resulting D-loop formation at the $R_1$ site blocks restriction cleavage by $R_1$ endonuclease. Therefore, the fragment treated with $R_1$ before complex formation will show separate A and B bands when analyzed by electrophoretic fractionation, whereas the filament complex fragment will show a single, larger molecular weight band. Methods for digesting DNA fragments with selected restriction endonucleases and analyzing the digest fragments by electrophoretic fractionation, for example, by Southern blotting, are well known.

Figure 7B:
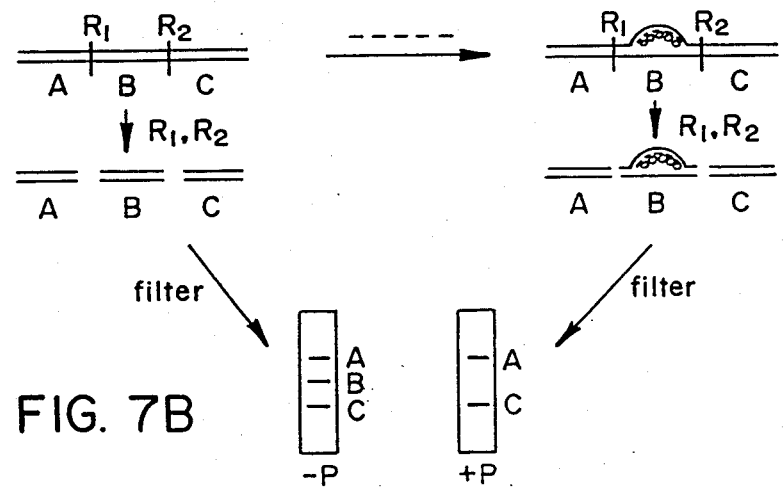

A variation of the method is illustrated in FIG. 7B. Here the filament probe P is homologous to a duplex region B between a pair of selected restriction sites $R_1$ (which separates regions A, B) and $R_2$ (which separates regions B, C).

The target DNA is mixed with a nucleoprotein filament whose single-strand DNA is homologous to region B only, to form a synaptic complexes between sites $R_1$ and $R_2$. After digestion with $R_1$ and $R_2$, the fragments are treated, for example, by selective binding to a glass fiber filter, to remove fragment complexes containing the probe filament. The nonhomologous fragments remaining are then analyzed by gel electrophoresis and compared to a control digestion in which no presynaptic filament was added. FIG. 2B shows the results from such an analysis, in which region B, having homology to the probe, is removed from the protected sample. This approach can also be combined with conventional Southern blot to analyze full genomic digests from uncloned DNA.

The restriction-fragment procedures just described provide a number of advantages over prior art methods. The hybridization can be carried out very rapidly, on the order of 30 minutes, as compared with many hours for conventional hybridization. In addition the number of steps required are greatly reduced, as the target DNA does not have to be denatured and attached to a solid support as the usual procedure is done in the prior art. Further, the duplex fragments in the fractionating gel can be detected by staining with ethidium bromide, so radiolabeled DNA is not required.

Finally, the results from the blocked restriction site analysis are qualitatively different from those from conventional methods, such as Southern blot analysis. The present method allows one to deduce which fragments are next to one another, based on the sizes of the new bands containing blocked restriction sites.

C. RecA Facilitated Clone Construction

Most recombinant vector constructions involve cloning a restriction fragment into a selected restriction site in a vector. Often the vector has two or more of the selected restriction sites, and this makes the construction much more difficult, in that a partial digest must be prepared and the correct construct selected from a mixture of incorrect constructs.

Figure 8:
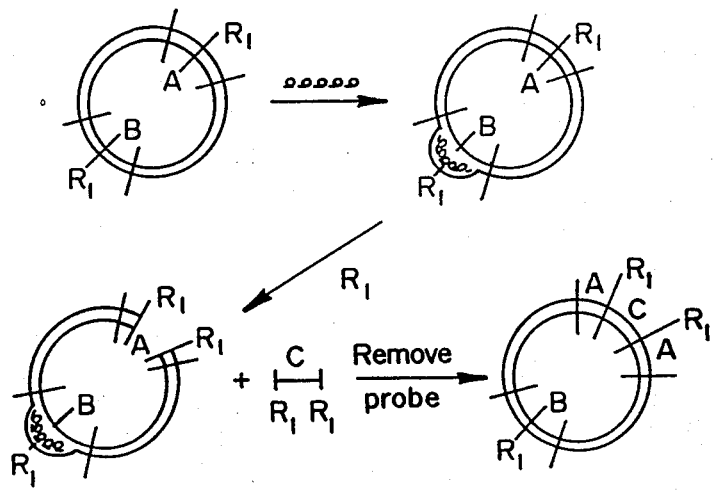
FIG. 8 shows how the filament of the invention can be used to simplify cloning vector construction.

A method of selectively blocking a restriction site in a cloning vector, according to the invention, is illustrated in FIG. 8. The vector shown contains two $R_1$ restrictions sites, one located in a region A into which heterologous DNA is to be inserted and a second located in a region B that is to be protected. To prepare a single-strand probe homologous to region B, a map of the cloning vector is examined for convenient restriction sites flanking the $R_1$ site in the B region. The vector is digested at these sites, and the expected size fragment is purified by conventional methods. The fragment is made single-stranded and used in forming a RecA nucleoprotein filament, as above.

The blocking filament is added to the vector, to form a synaptic complex that will inactivate the B-region $R_1$. The vector, with its unblocked A-region $R_1$ site, is then linearized at A with $R_1$ restriction enzyme. After cleavage, the DNA is deproteinized and resuspended in low salt to remove the probe sequences from the D-loops by branch migration. From this point on, the procedure for subcloning is identical to the conventional procedures, with the desired fragment being introduced, and the vector ligated as indicated.

The method allows vector constructions to be made from a much larger number of restrictions sites in vectors, with greatly reduced effort devoted to selecting correct constructions from incorrect ones.

D. Rapid Screening of Minilysate Preparations for Probe Sequence

Currently, many vectors are screened by analyzing a small sample of DNA (minilysate preparation) from many different clones by size or by blot hybridization to determine if they contain a desired sequence (reference 11). This section describes a more rapid and convenient screening procedure using the nucleoprotein filament of the invention.

In the screening procedure, a nucleoprotein filament is made with a probe that contains a sequence homologous to the sequence which may be present in the clone being analyzed. The filament is then added to each of the minilysates to form homologous-region synaptic complexes. These complexes are filtered on glass fiber filters, and the DNA eluted and analyzed by gel electrophoresis, as described above. Those tracks with DNA in them contain samples homologous to the probe sequence. Alternatively, the filaments can be made with a radioactive probe and after synapsis, the reaction mixture can be treated with S1 nuclease and precipitated with trichloracetic acid and precipitate counted for radioactivity. Only preparations with homologous sequences to the probe would be positive.

From the foregoing, it can be appreciated how various objects and features of the invention are met. The nucleoprotein filament of the invention is stable, efficient in synaptic complex formation, and readily formed in a low-$Mg^{++}$ medium without a requirement for SSB. The stability of the complex does not depend on continued ATP supply, and the filament, once formed, can be stored frozen over extended periods.

The filament, when added to homologous target duplex DNA, efficiently and rapidly forms a stable synaptic complex which permits a number of unique applications to purifying, analyzing, and manipulating duplex fragments and vectors.

The following examples illustrate procedures for preparing and using the nucleoprotein filament of the invention. The examples are intended to illustrate, but not limit, the scope of the invention.

Materials and Reagents

RecA protein (RecA) was purified as described in reference 15, and prepared as a 25 $\mu$M solution in 50 mM Tris-HCl, pH 7.5, 1 mM dithiothreitol (DTT), 0.3 mM EDTA, and 10% glycerol. Proteinase K was obtained from Sigma Chem Co. (St. Louis, MO), and prepared as a 3 mg/ml solution in distilled water. ATP$\gamma$S, obtained from Boehringer Mannheim (Indianapolis, IN), was prepared in 10 mM Tris-HCl, pH 7.5, 2 mM DTT, and stored at $-20°$ C. Whatman GF/C 2.4 cm glass microfiber filters were supplied by Whatman (Clifton, NJ). Creatine phosphokinase was obtained from Sigma Chem. Co. Buffer A (10X) contained 310 mM Tris-HCl, pH 7.5, 10 mM $MgCl_2$, and 4 mM DTT. Phenol was equilibrated with 10 mM Tris-HCl, pH 8.0 (Maniatis).

EXAMPLE I

Preparing Nucleoprotein Filaments

Circular single strand DNA (viral form) from phage M13 and $\phi$X174 was prepared as described in reference 22. The M13 DNA was dissolved in 10 mM Tris-HCl, pH 7.5, containing 1 mM EDTA, to 380 $\mu$M, and the $\phi$X174, to 941 $\mu$M in the same buffer.

ATP$\gamma$S filaments were prepared by mixing 1.2 mM ATP$\gamma$S, 7.25 $\mu$M RecA, 20 $\mu$M single stranded DNA in 1X Buffer A, at 37° C. for 10 min. ATP filaments were similarly prepared, but substituting 1.2 mM ATP for ATP$\gamma$S, and including 6 mM phosphocreatine and 10 U/ml creatine phosphokinase as an ATP generating system. The reactions were performed in 1.5 ml Eppendorf tubes set in a 37° C. water bath, at a total reaction volume of 0.5 ml.

EXAMPLE II

Preparing DNA Substrate

Circular replicative form DNA (tritium labelled) from phage $\phi$X174 was prepared as described in reference 18, and linearized at a unique PstI site. DNA from phage lambda was purchased from Boehringer Mannheim, and digested to completion with PvuII, which cuts the phage at 15 sites.

A duplex DNA mixture was prepared by mixing in a separate tube: 1.0M MgCl (12.4 $\mu$l), 2.65 mM PvuII-digested lambda DNA (142 $\mu$l), and 634 $\mu$M tritium-labeled $\phi$X174 PstI-digested DNA (6 $\mu$l). The final substrate mixture contains a 100:1 molar ratio of unlabeled phage DNA to labelled $\phi$X174.

EXAMPLE III

Pairing Reaction with Homologous and Heterologous DNA

This section examines the specificity of binding of the $\phi$X174 and M13 nucleoprotein filaments from Example I with the duplex $\phi$X174 substrate mixture from Example II.

The substrate mixture from Example II was added to each of the labelled filament mixtures to a final duplex DNA concentration of about 3.5 $\mu$M tritium $\phi$X174 DNA and 350 $\mu$M phage DNA, and $MgCl_2$ was added to a final concentration of 12.5 mM. The combined volume of the additions to the 0.5 ml filament samples was less than 100 $\mu$l. The reaction mixture was vortexed, and incubated in a 37° C. water bath for 30 min.

A 200 $\mu$l aliquot from each of the two samples was diluted to 4 ml with cold distilled water, and stored on ice for 2–5 min. The diluted mixture was filtered through a Whatman GF/C filter on an aspirator filtration device. The filters were wetted with water immediately before use. The aspirator was adjusted to draw the 4 ml sample through the filter in 2–5 sec. The sample tubes were rinsed with cold distilled water, and the rinse was passed through the filters.

To determine total radioactivity, a 40 $\mu$l aliquot from each of the samples was spotted on a Whatman GF/C filter. The filters were dried and counted in 4 ml of a standard scintillation fluid.

In the sample containing homologous $\phi$X174 filament and $\phi$X174 labelled duplex substrate, about 52% of the total sample counts were retained on the filter. Only about 1.7% of the total counts were retained in the sample containing heterologous M13 filament and $\phi$X174 labelled duplex DNA. These results indicate that (1) at least about 52% of the possible triple-strand complexes were formed in the complexing reaction and (2) the D-loop complexes were trapped efficiently and specifically on the glass fiber filter.

EXAMPLE IV

Recovery of Homologous DNA Retained by Filter

The two samples from Example III were each filtered, as above, by passing diluted, 4 ml samples through a Whatman GF/C filter. Immediately after filtration, the filters were removed and placed in a 1.5 ml Eppendorf tube without wadding or folding. To each tube was added 0.9 ml of distilled water and 0.1 ml of proteinase K, 3 mg/ml. The tubes were incubated at 37° C. for 30 min, then heated to 65° C. for 20 min, vortexing briefly every 5 min at the higher temperature. The filter was removed, dried, and counted for tritium label as in Example III.

The Eppendorf tubes containing the filter extracts were centrifuged 5 min at low speed to remove filter material, and the liquid carefully removed and transferred into 15 ml polypropylene tubes. Phenol (1 ml) was added to each tube, the mixture vortexed, and centrifuged at low speed for 5 min. The upper aqueous phase from the phenol extraction was ether extracted 5 times, and the aqueous phase was then concentrated by successive extractions with 3 ml, 1 ml, and 0.15 ml volumes of n-butanol. The upper phase in each case was discarded after centrifugation. The aqueous volume was now reduced to about 20–30 $\mu$l. This material was ether extracted 3 times, and the ether evaporated in a desiccator. The extracted DNA was counted for tritium label in 4 ml of a standard scintillation fluid.

Approximately 45% of the homologous DNA (from the pairing of φX174 filaments with φX174 duplex substrate) was recovered in the filter extract. About 4.5% remained on the filter. From the small fraction of heterologous DNA (the pairing of M13 filaments with the φX174 duplex substrate) which bound to the filter, about 0.7% total counts were recovered in the filter extract and about 0.2% remained bound to the filter. The enrichment of homologous duplex is therefore about 45%/0.7%, or about 64 fold. The percentage of homologous DNA in the enriched fraction is now about 39%.

EXAMPLE V

Enrichment of Homologous DNA in a 1000X Dilution

The pairing and filtration method described in Examples III and IV was applied to a homologous sample (φX174 duplex substrate) diluted 1:1000 with phage lambda. Employing the same procedures, a 43% retention of homologous DNA and a 1.2% retention of heterologous DNA on the filters was observed. This approximately 35 fold enrichment translates, for a 0.1% sample, to a final concentration of about 3.5% homologous DNA. Assuming similar recovery in a second round of RecA pairing, the homologous DNA would have a final concentration of about 57%, i.e., two rounds would yield a 570-fold enrichment. One enrichment procedure performed with the 1:100 DNA mixture from Example III gave 94% recovery of homologous DNA after a first round of enrichment and 80% recovery after a second round, i.e., a final recovery of about 75% of the total homologous DNA after two rounds. This data indicates that multiple rounds of enriching can be carried out without a severe loss of target duplex material.

EXAMPLE VI

RecA Binding to ssDNA-Method 2

A probe solution containing a selected quantity of single-strand pBR322 which was $^{32}$P-labeled by nick translation, producing fragments of about 1.6 kbase median length, or, alternatively, a single-stranded LN11A, a 6.5 kbase MHC pseudogene which was $^{32}$P-labeled and biotinylated by nick translation, was added to an Eppendorf tube, along with 2 μl of nuclease-free bovine serum albumin (5 μg/μl in 10 mM TE (Tris-HCl, 1 nM EDTA) buffer, and the final volume was adjusted to 90 μl with 10 mM T.E., pH 8.0. After boiling for 5 min the solution was chilled on ice for 5 min and centrifuged for a few seconds. 10 μl of freshly made 10×buffer (20 mM CoCl$_2$, 16 mM ATPγS, 80 mM MgCl$_2$, 300 mM Tris-Cl, pH 8) and the appropriate amount of RecA was added, vortexed lightly and incubated at 37° C. for 10 min. Heterologous or homologous double stranded DNA was then added and the tube was vortexed lightly and incubated for 10 min.

For electrophoretic examination of the reaction product, a 10 μl sample of the final reaction mixture was added to prechilled Eppendorf tubes containing 10 μl 1×electrophoresis buffer/0.1% SDS (sodium dodecyl sulfate), vortexed and electrophoresed in a 0.8% agarose gel, which was subsequently autoradiographed.

A. Reaction Requirements

The complexing reaction above was examined for (a) RecA requirement, (b) probe specificity, (c) and complex formation involving biotinylated probes. The results are discussed with reference to FIG. 3, which shows electrophoretic patterns obtained in various reaction mixtures.

In FIG. 3A, 10 fmoles of the pBR322 probe were used in the complexing reaction described above, where the concentration of RecA used was 1 μM. Lane 1 shows labelled ds pBR322 (1.6 nM); lane 2, probe alone, lane 3, no RecA, and lane 4, substituting heterologous ds M13 (2 nm) for ds pBR322. As seen, only lane 1 is labelled, indicating that:the labelled band is not due to probe alone (lane 2); the complexing reaction requires RecA (lane 3); and the reaction is highly specific for homologous target duplex DNA.

The migration patterns of ds pBR322 and M13 in non-complexed form, and stained with ethidium bromide, are shown in FIG. 3B, lanes 1 and 2, respectively. Assuming that the different bands in lane 1 represent different topological forms of pBR322, it is seen from FIG. 3A, lane 1, that the probe/RecA filament reacts with both forms.

In a second series of reactions, the radiolabeled pBR322 probe used was also biotinylated with Bio-11-dUTP (Brigati), according to methods described in Example VII below. The results are shown in FIG. 3C. Lane 1 shows labelled ds pBR322 complexed with $^{32}$P-labeled, biotinylated pBR322 probe/RecA (lane 1) and probe/RecA alone (lane 2). A comparison of FIGS. 3A and 3C indicates little or not effect of the biotin label on complex formation.

FIG. 3D shows the electrophoretic patterns of a probe/duplex target compolex formed by reacting 21 fmoles of the LN11A probe with 1 μM Rec A, as above, and then 11 nM cos 6, a 38 kbase recombinant cosmid containing LN11A as part of its insert. The probe/cosmid complex is indicated by the arrow in lane 1. Lane 2 shows the pattern of the probe alone.

B. RecA Binding Parameters

Complex reactions between ds pBR322 and the above $^{32}$P-labeled and biotinylated pBR322 probe were carried out as above, under conditions of variable ds pBR322, variable RecA concentration, variable probe concentrations, and increasing times.

The first series of reactions contained 8 fmoles of the probe, 1 μM RecA, and increasing concentrations of ds pBR322. Following the complexing reaction, 10 μl of reaction mixture was fractionated by SDS gel electrophoresis as above. The results are shown in FIG. 4A for ds pBR322 concentrations of 0.0032 nM (lane 1), 0.016 nM (lane 2), 0.032 nM (lane 3), 0.1 nM (lane 4), and 0.32 nM (lane 5). The position of the probe/target complex is indicated by the arrow in the figure. The complex is seen faintly at 0.1 nM, and clearly at 0.32 nM.

In the second series of reactions, the probe concentration was 8 fmole, the ds pBR322 concentration, 0.32 nM, and the RecA varied. The resulting probe/target electrophoretic patterns are seen in FIG. 4B, for reactions in which the RecA concentration was: 0.08 μM (lane 1), 0.16 μM (lane 2), 0.32 μM (lane 3), 0.64 μM (lane 4), 1.28 μM (lane 5), 2.56 μM (lane 6), and 5.12 μM (lane 7). The position of the probe/target complex is indicated by the arrow, as above. As seen from the relative intensity of the complex, the reaction shows a biphasic response with increasing RecA concentration, increasing to a maximum at about 0.32 μM, and falling off dramatically below about 0.16 μM, and above about 0.64 μM.

The third series of reactions shows the dependence of the increasing amounts of probe, at a fixed concentration of target ds pBR328 (0.032 nM) and RecA (1 μM). FIG. 4C shows the electrophoretic patterns of probe/target complex at probe concentrations of 0.14 fmoles (lane 1), 0.71 fmoles (lane 2), 1.4 fmoles (lane 3), 2.9 fmoles (lane 4), 4.3 fmoles (lane 5), 5.7 fmoles (lane 6), and 5.12 fmoles (lane 7). It is clear that increasing amounts of probe give increasing amounts of probe/target complex (indicated by the arrow).

In the fourth series of tests, the probe/target complex reaction was carried out as above, with 7.2 fmoles probe, 1 μM RecA, and 0.32 nM ds pBR328. Aliquots were taken at increasing reaction times and and fractionated by SDS gel electrophoresis. The gel patterns are seen in FIG. 4D for reaction times of 1 min (lane 1), 2 min (lane 2), 3 min (lane 3), 5 min (lane 4), and 10 min (lane 5). The gel patterns indicated that the complex reaction is essentially complete after 1 minute.

EXAMPLE VII

Preparation of Biotinylated Probes

Double-stranded (ds) probes were biotinylated according to one of four methods detailed below, then denature conventionally to form single-strand (ss) probes. The biotinylated nucleotides used were Bio-11-dUTP (Brigati) which have an 11-atom linker arm separating the biotin and the pyrimidine base, and Bio-19-SS-dUTP (Herman) which have a 19-atom linker containing a disulfide bond. $^{32}$P-labeled dNTPs were included when monitoring of the various steps of the method was desirable. The nick-translation method (A) was preferred for probes greater than about 1 kbase in size; the end labeling methods (B-D), for shorter probes.

A. Nick-translation

A typical reaction, carried out in 60 μl final volume, contained 1 μg DNA in 50 mM Tris-Cl pH 7.5, 10 mM MgSO4, 0.1 mM DTT,, 100 mM of each of the following nucleotides dATP, dGTP, and Bio-11-dUTP or Bio-19-SS-dUTP (gift from Dr. T. Herman), 120 μCi of $[\alpha-^{32}P]$ dUTP (Amersham, specific activity 3,000 Ci/mmole), 30 U DNA polymerase I (New England Biolabs), and 27 pg/ml DNAse I (Sigma). The reaction mixture was incubated at 14° C. for one hour, stopped by addition of EDTA to 10 mM and heated at 68° C. for 5 min. Labeled DNA was recovered by chromatography over Sephadex G50 (Pharmacia) equilibrated and eluted with 10 mM Tris-Cl, pH 7.5/1 mM EDTA (T.E.). When large amounts of probe were required for multiple reactions two to three nick-translations were run in parallel and loaded onto one column to obtain a concentrated probe solution.

B. Tailing by terminal transferase

This was used only for DNA molecules having 3' protruding ends. The reaction consisted of 1 μg DNA in 100 mM potassium cacodylate (pH 7.2), 2 mM CoCl2, 0.2 mM DTT, 100 μM Bio-11-dUTP, 50 μCi $[\alpha-^{32}P]$ dCTP, and 20 U terminal transferase, added last. After incubation at 37° C. for 45 min, an additional 20 U of enzyme was added and the incubation repeated. The reaction was terminated by EDTA added to 10 mM, the DNA was recovered as described above, precipitated with ethanol, washed with 70% ethanol and resuspended in 50 μl of T.E.

C. Labeling by T4 DNA polymerase replacement reaction

The reaction contained 1 μg of DNA in 33 mM Tris-OAc (pH 7.9), 66 mM NaOAc, 10 mM MgOAC, 0.5 mM DTT, 0.1 mg/ml BSA, and 0.5 U T4 DNA polymerase (P-L Biochem). After incubation at 37° C. for 7 minutes, dATP, dGTP, and Bio-11-dUTP were added to a final concentration of 150 μM, dCTP was added to 10 μM, 50 μCi of $[\alpha-^{32}P]$ dCTP (3000 Ci/mmole), and TrisOAc, NaOAc, MgOAc, BSA, and DTT were added to maintain previous concentrations. This reaction was incubated at 37° C. for 30 min, then dCTP was added to a concentration of 150 μM, and the reaction incubated for an extra 60 min at 37° C. The reaction was stopped by addition of EDTA to 10 μM, heated at 65° C. for 10 min, chromatographed and processed as described before.

D. Klenow fill-in reaction

This was carried out following standard protocols (Maniatis); incubation was at room temperature for 15 min.

EXAMPLE VIII

Target Purification by Streptavidin Chromatography

Buffers: Buffer A: 10 mM Tris-Cl, pH 7.5/1 mM EDTA/0.3M NaCl/10 μg/ml salmon sperm DNA (phenol extracted and sonicated). Buffer B: 10 mM Tris-Cl, pH 7.5/1 mM EDTA/50 mM NaCl. Buffer C: 30 mM Tris-Cl, pH 8.8/0.1 mM EDTA/50 mM DTT (freshly made). Streptavidin-agarose was obtained from Bethesda Research Labs (Bethesda, MD), and silanized 1 ml disposable syringes, from Becton-Dickinson, Rutherford, NJ).

The chromatography procedure was applied to the probe/RecA/target duplex reaction mixture described generally in Example VI. A 1 ml silanized syringe plugged with silanized glass wool was packed with 0.3 ml streptavidin-agarose and washed with Buffer A. Following addition of proteinase K and SDS to the RecA reaction mixture to final concentrations of 0.2 mg/ml and 0.2% respectively, the mixture (containing proteinase K and SDS) was incubated for 7 min at 37° C. and immediately loaded onto the column which was then eluted in sequence with Buffer A (10 1-ml fractions), Buffer B (2 1-ml fractions) and Buffer C (one 5-ml fraction), each collected in a polypropylene tube. The final 5 ml fraction was monitored for amount of target DNA present as described below in this example, or and/or for ability to transform bacterial host cells, for purposes of further separating target and non-target DNA, as described below in the next example.

Linear LN11A was biotinylated with Bio-19-SS-dUTP (EXAMPLE VII), but not radiolabeled, by nick translation, converted to single-strand form, and reacted in the presence of RecA with 0.12 nM homologous ds pLN11A (Tet$^r$, Kan$^s$) and 24 SV40 viral DNA, and in a second reaction, with 27 nM heterologous ds pMK102 (Tet$^s$, Kan$^r$). Each reaction mixture was chromatographed on a streptavidin column, as above. Control reactions with radiolabeled probe were used to follow complex probe/target complex formation. Portions of each column fraction were dot-blotted on nitrocellulose filter paper, and the amount of plasmid DNA quantitated by hybridization to $^{32}$P-labeled ss pBR328, which hybridizes to pLN11A, but not SV40. The elution profiles for the RecA reaction with ds pLN11A and ds pMK102, expressed as percent of total plasmid DNA participating in each reaction, are shown in solid and open circles, respectively, in FIG. 5. Over 99% of the heterologous plasmid was eliminated in the first three fractions while only traces were present in fractions 13 to 16, which contain the recovered homologous plasmid. Two thirds of the homologous plasmid was found in fraction 1 along with about 10% of the probe, the latter being assessed by the distribution of its radioactivity. The remaining one third was recovered from the column following treatment with DTT (fractions 13 to 16; (these fractions also contained 80% of the probe). It is clear from the figure that the method achieves purification by the combination of quantitative elimination of the heterologous plasmid in the early flow-through fractions and selective retention and subsequent release of the homologous plasmid-probe complexes.

The fractions eluted with Buffer C were used for *E. coli* transformation. A portion of the transformation mixture was plated on a tetracycline plate (which allows growth of cells transformed with the probe-homologous pLN11A plasmid), and an equal portion, kanamycin plate (which allows growth of cells transformed with the probe-heterologous pMK102 plasmid). Appropriate transformation control were run in parallel. The number of transformants of each type produced were counted, and used to determine the ratio of homologous/heterologous plasmids at each elution point. The average degree of DNA enrichment was measured by the ratio of homologous to heterologous DNA in the initial and purified samples. The average enrichment for six experiments was about $10^{4.6}$. The total recovery of homologous DNA, also measured by total number of transforming plasmids, range between about 10-20%, with an average for six experiments of about 14.3%.

EXAMPLE IX

Target Purification by $Cu^{++}$ Chelate Chromatography

Buffers: Buffer A: 20 mM $NaHCO_3$/1M NaCl/10 µg/ml of salmon sperm DNA (phenol extracted and sonicated). Buffer B: 20 mM $NaHCO_3$/50 mM NaCl. Buffer C: 50 mM EDTA pH 7.5/50 mM NaCl. All buffers were freshly prepared. Avidin-DN was obtained from Vector Laboratories (Burlingame, CA); and iminoacetic acid-agarose from Pierce Chemical Co. (Rockford, IL).

Prior to column chromatography, avidin-DN and 5M NaCl were added to the RecA reaction mixture (Example VI) to final concentrations of 0.22 mg/ml and 1M, respectively, and incubated at room temperature for 1-2 hrs with gentle shaking every 10-20 min. Longer incubations were required when only one or two biotinylated nucleotides were present per probe molecule. Avidin concentrations between 0.02 and 0.36 mg/ml gave maximal complex retention by the column.

A silanized 1 ml syringe was packed with 9.3 ml of iminodiacetic acid-agarose and washed in sequence with 10 column volumes of autoclaved $dH_2O$, 0.16 ml of $CuSO_4$ (5 mg/ml in $dH_2O$, filter sterilized), and 10 column volumes Buffer A. The sample was loaded and the column was eluted in sequence with Buffer A (5 1-ml fractions), Buffer B (2 1-ml fractions) and Buffer C (2 1-ml fractions). Eluted fractions were diluted 6-fold with autoclaved $dH_2O$, heated at 68° C. for 10 min, phenol extracted once by gently mixing the two phases, butanol concentrated to 0.2-1 ml and dialyzed overnight at 4° C. against 1 mM Tris-Cl, pH 7.5/0.1 mM EDTA/5 mM NaCl. The samples were then concentrated under negative pressure (Speed Vac) to about 100 µl and used for *E. coli* transformation.

The chromatography procedure was applied to a probe/RecA/target reaction mixture containing a LN11A probe which had been radiolabeled and biotinylated by end labeling. Specifically, protruding 5' ends of the LN11A were reconstituted by a Klenow fill-in reaction using both $^{32}P$-dATP and Bio-11-dUTP. The RecA reaction mixture included 0.0124 pmoles of pLN11A (Tet$^r$, Kan$^s$) and 2.72 p moles pMK102 (Tet$^s$, Kan$^r$) (ratio of homologous:heterologous DNA of 1:219). This mode library offers two advantages: first, the fate of each plasmid during screening can be monitored biologically by transformation owing to their differential antibiotic sensitivities; and second, pMK102 and LN11A, being totally heterologous, do not form base-pair complexes with each other.

The reaction was carried out as in Example VIII, and the reaction mixture was chromatographed as above, and the radioactivity associated with each fraction (due to the presence of radiolabeled probe) determined by Cherenkov counting. The probe counts are indicated by vertical dashed lines in FIG. 6. As seen, the bulk of the probe label is eluted with the EDTA buffer.

Fractions 1-5 were desalted by passage over G50 Sephadex, then processed as fractions 6-8. Portions of each fraction were used for *E. coli* transformation. Half of the transformation mixture was plated on a tetracycline plate (which allows growth of cells transformed with the probe-homologous pLN11A plasmid), and kanamycin plate (which allows growth of cells transformed with the probe-heterologous pMK102 plasmid). Appropriate transformation control were run in parallel. The number of transformants of each type produced at each elution point were counted, and used to determine the ratio of homologous/heterologous plasmids at each elution point. The results are shown in FIG. 6. As seen, the method enriches the homologous DNA, as measured by number of number of transforming plasmids, by nearly $10^5$, from less than $10^{-2}$ to greater than $10^2$. Total recovery of homologous DNA for several experiments was between 10%-20%. The enrichment and recovery of homologous DNA is thus similar to that observed with the streptavidin column method described in Example VIII.

While preferred embodiments of preparing and using the nucleoprotein filament of the invention have been described, it will be apparent to those in the art that various modifications and changes can be made without departing from the invention.

What is claimed is:

1. A method of separating target and non-target duplex DNA molecules on the basis of a selected base sequence which is unique to the target sequence, comprising providing stable, single-stranded nucleoprotein filaments, each composed of a single-stranded DNA probe having a region of homology with the selected base sequence, and RecA protein molecules bound stably to the DNA probe, in the presence of adenosine 5'-(γ-thio)triphosphate, reacting the filaments with the target and non-target DNA molecules under conditions which promote rapid homologous alignment between the probe and homologous target base sequences in the reaction mixture, with formation of a stable filament/target complex, contacting the reaction mixture with a solid support designed to selectively bind target molecules which are complexed with said filaments by such homologous alignment, removing non-bound DNA molecules from the support, and treating the support to release target DNA molecules which are selectively bound to the support through such complex formation.

2. The method of claim 1, wherein the filaments provided are formed by reacting the probe with RecA protein in the presence of adenosine 5'-(γ-thio)triphosphate, at a concentration of at least about 0.5 mM, and $Mg^{++}$, at a concentration of between about 0.5 and 2 mM, and said reacting is carried out at a $Mg^{++}$ concentration of greater than about 4 mM.

3. The method of claim 1, for use in separating circular target DNA from a mixture of circular target and non-target molecules, wherein said providing includes reacting a such probe with adenosine 5'-(γ-thio)triphosphate in the presence of up to 10–20 mM $Mg^{++}$, and an amount of RecA whose concentration is selected on the basis of the total amount of DNA in the reaction mixture, to give optimal or near-optimal complex formation by said reacting.

4. The method of claim 1, wherein the target DNA is a vector capable of transforming a suitable bacterial host, and containing a selectable marker by which host cells transformed with the target DNA can be distinguished from host cells transformed with non-target DNA, which further includes transforming such host cells with the released target DNA and selecting transformed cells containing the selectable marker.

5. The method of claim 1, wherein the filament contains biotin molecules which are derivatized to probe nucleotides through disulfide linkages, the reaction mixture is contacted with a solid support containing surface bound avidin, streptavidin, or an analog thereof, and said treated includes releasing bound complex material by washing the solid support with a mild reducing agent effective to cleave disulfide bonds.

6. The method of claim 1, wherein the filament contains covalently bound biotin which is also bound to avidin, streptavidin, the reaction mixture is contacted with a solid support containing surface bound iminodiacetic acid acid moieties in the presence of $Cu^{++}$, and said treating includes washing the solid support with a chelating agent effective to remove $Cu^{++}$ from support.

7. A method of forming a stable, single-stranded nucleoprotein filament effective to complex stably and specifically with a target duplex DNA having a selected base sequence, said method comprising providing a single-stranded DNA probe having a region of homology with such selected base sequence, and reacting the DNA probe with RecA protein in the presence of adenosine 5'-(γ-thio)triphosphate at a $Mg^{++}$ concentration of less than about 10–20 mM.

8. The method of claim 7, wherein the $Mg^{++}$ concentration is between about 0.5–2 mM, and the concentration of adenosine 5'-(γ-thio)triphosphate is at least about 0.5 mM.

9. A system for separating target and non-target duplex DNA molecules on the basis of a selected base sequence which is unique to the target sequence, comprising stable, single-stranded nucleoprotein filaments, each composed of a single-stranded DNA probe having a region of homology with the selected base sequence, said filaments having a biotin/avidin complex formed by binding avidin, streptavidin, or an analog thereof with biotin, said complex derivatized to the probe nucleotides through disulfide linkages, and said filaments having RecA protein molecules bound stably to the DNA probe, in the presence of adenosine 5'-(γ-thio)triphosphate, to promote rapid homologous alignment between the probe and homologous target base sequences, with formation of a stable filament/target complex, and a solid support, designed to selectively bind target molecules, with surface-bound binding molecules effective to selectively bind biotin/avidin complexes to the support when the filaments are complexed by such homologous alignment to such target sequences, wherein said binding molecules are iminodiacetic acid moieties which are effective to bind to such biotin/avidin complexes in the presence of $Cu^{++}$.

10. A system for separating target and non-target duplex DNA molecules on the basis of a selected base sequence which is unique to the target sequence, comprising stable, single-stranded nucleoprotein filaments, each composed of a single-stranded DNA probe having a region of homology with the selected base sequence, said filaments having biotin derivatized to the probe nucleotides through disulfide linkages and said filaments having RecA protein molecules bound stably to the DNA probe, in the presence of adenosine 5'-(γ-thio)triphosphate, to promote rapid homologous alignment between the probe and homologous target base sequences, with formation of a stable filament/target complex, and a solid support, designed to selectively bind target molecules, with surface-bound binding molecules effective to selectively bind biotin to the support when the filaments are complexed by such homologous alignment to such target sequences, wherein said binding molecules are avidin, streptavidin, or analogues thereof.

11. A stable, single-stranded nucleoprotein filament effective to complex specifically and stably with a target duplex DNA having a selected base sequence, in the absence of single-strand binding protein, said filament comprising a single-stranded DNA probe having a region of homology with such selected base sequence, wherein said probe is derivatized with one or more ligands effective to bind specifically and with high affinity to binding molecules carried on a solid support, when the filament is complexed with target duplex DNA, and RecA protein molecules bound stably to the DNA probe in the presence of adenosine 5'-(γ-thio)triphosphate.

12. The filament of claim 11, wherein the ratio of RecA molecules to nucleotide residues in the probe is between about 1:3 and 1:6.

13. The filament of claim 11, wherein the RecA protein is derived from *E. coli*.

14. The filament of claim 11, wherein the ligands are biotin molecules derivatized to probe nucleotides for use with (a) a solid support containing surface attached avidin, streptavidin, or analogues thereof, where the biotin is linked to the nucleotides through disulfide linkages, and (b) a solid support having surface-bound iminodiacetic acid moieties, where the biotin is also complexed with avidin, streptavidin, or an analog thereof.

* * * * *